(12) United States Patent
Reynolds

(10) Patent No.: US 9,023,888 B2
(45) Date of Patent: May 5, 2015

(54) COMPOSITION OF MONOTERPENOIDS HAVING BACTERICIDAL PROPERTIES

(76) Inventor: Max Reynolds, Kuraby (AU)

( * ) Notice: Subject to any disclaimer, the term of this patent is extended or adjusted under 35 U.S.C. 154(b) by 0 days.

(21) Appl. No.: 13/983,492

(22) PCT Filed: Aug. 19, 2011

(86) PCT No.: PCT/GB2011/001239
§ 371 (c)(1),
(2), (4) Date: Oct. 4, 2013

(87) PCT Pub. No.: WO2012/104570
PCT Pub. Date: Aug. 9, 2012

(65) Prior Publication Data
US 2014/0039045 A1 Feb. 6, 2014

(30) Foreign Application Priority Data

Feb. 2, 2011 (GB) .................................... 1101778.7
Mar. 1, 2011 (GB) .................................... 1103502.9

(51) Int. Cl.
| | | |
|---|---|---|
| *A61K 31/35* | (2006.01) | |
| *A61K 31/045* | (2006.01) | |
| *A61K 31/047* | (2006.01) | |
| *A61K 31/122* | (2006.01) | |
| *A61K 31/125* | (2006.01) | |
| *A61K 31/336* | (2006.01) | |
| *A61K 31/343* | (2006.01) | |
| *A61K 31/357* | (2006.01) | |
| *A61K 31/015* | (2006.01) | |
| *A61K 45/06* | (2006.01) | |
| *C07C 15/085* | (2006.01) | |
| *C07C 35/14* | (2006.01) | |
| *C07D 493/08* | (2006.01) | |

(52) U.S. Cl.
CPC ............. *A61K 31/35* (2013.01); *A61K 31/045* (2013.01); *A61K 31/047* (2013.01); *A61K 31/122* (2013.01); *A61K 31/125* (2013.01); *A61K 31/336* (2013.01); *A61K 31/343* (2013.01); *A61K 31/357* (2013.01); *A61K 45/06* (2013.01); *A61K 31/015* (2013.01); *C07C 15/085* (2013.01); *C07C 35/14* (2013.01); *C07D 493/08* (2013.01)

(58) Field of Classification Search
CPC ... A61K 31/35; A61K 31/045; A61K 31/047; A61K 31/122; A61K 31/125; A61K 31/336; A61K 31/343; A61K 31/357; A61K 31/015
USPC ....................................................... 514/456
See application file for complete search history.

(56) References Cited

U.S. PATENT DOCUMENTS

| | | | |
|---|---|---|---|
| 5,110,832 A | 5/1992 | Chastain et al. | |
| 5,294,645 A | 3/1994 | Chastain et al. | |
| 5,543,435 A | 8/1996 | Chastain et al. | |
| 6,759,370 B1 * | 7/2004 | Innes ............................ | 504/142 |
| 2010/0092398 A1 | 4/2010 | Reynolds | |

FOREIGN PATENT DOCUMENTS

| | | |
|---|---|---|
| EP | 1 982 705 A1 | 10/2008 |
| WO | 94/08551 A2 | 4/1994 |
| WO | 2011/045557 A1 | 4/2011 |

OTHER PUBLICATIONS

Barton et al. ("Herbicidal Activity of Cineole Derivatives" J. Agric. Food Chem. 2010, 58, 10147-10155).*
International Search Report and Written Opinion dated Jun. 21, 2012 from PCT/GB2011/001239; 15 pages.
Written Opinion dated Feb. 18, 2013 from PCT/GB2011/001239; 14 pages.
IPRP dated May 17, 2013 from PCT/GB2011/001239; 15 pages.

* cited by examiner

*Primary Examiner* — Yong Chong
(74) *Attorney, Agent, or Firm* — Ohlandt, Greeley, Ruggiero & Perle, L.L.P.

(57) ABSTRACT

A composition having bactericidal properties comprising; (a) 30%-80% of at least one compound having the formula (I) and (b) 10% to 40% of at least one compound of formula (II)

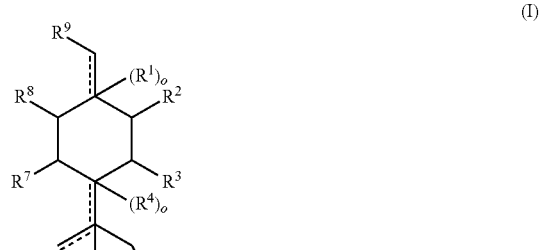

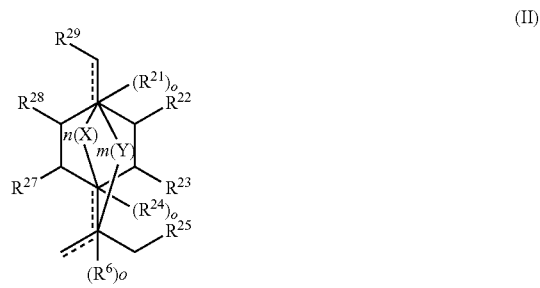

16 Claims, No Drawings

COMPOSITION OF MONOTERPENOIDS HAVING BACTERICIDAL PROPERTIES

FIELD OF THE INVENTION

The present invention relates to a composition having bactericidal properties suitable for a wide variety of therapeutic uses such as an antiviral, antibacterial or antifungal agent. In particular, the present invention is directed towards a composition suitable for internal administration in an animal.

BACKGROUND OF THE INVENTION

Essential oils are generally obtained by steam distillation of parts of a source plant. The oils are complex mixtures of hydrocarbons and some oils can contain more than a hundred different compounds. The majority of the compounds found in essential oils can be classified as monoterpenes, sesquiterpenes and their oxygenated derivatives thereof.

Monoterpenes are formed from two isoprene units and have the molecular formula $C_{10}H_{16}$ and may be acyclic, monocyclic or bicyclic. Biochemical modifications such as oxidation or rearrangement produce related compounds having a monoterpene skeleton. These derivatives are referred to as monoterpenoids. Some authors use the term monoterpene to refer to any compound having a monoterpene skeleton. However in the present specification and claims, the term monoterpene will be used to refer only to those compounds having the molecular formula $C_{10}H_{16}$.

Sesquiterpenes consist of three isoprene units and have the molecular formula $C_{15}H_{24}$. In the present specification and claims the term sesquiterpene will be used to refer to compounds having the $C_{10}H_{15}$ molecular formula and sesquiterpenoid to oxygenated derivatives of the sesquiterpenes.

The scientific and alternative medicine literature is replete with reports of the biological activity of essential oils. Many essential oils have been purported to have a range of antimicrobial, antiviral, anti parasitic and antifungal activity. Much of the alternative medicine literature is based upon anecdotal evidence of activity. Scientific studies are often confounded by the use of poorly characterised oils. The composition of essential oils may differ significantly between plant strains, plant part, country of origin, season, storage conditions and the like. Of particular interest is the reported activity of some essential oils against antibiotic resistant bacteria. Particularly problematic is the emergence of methicillin resistant *Staphylococcus aureus* (MRSA). A number of essential oils have been shown to be effective against MSRA. A 5% tea tree oil has been reported as an effective body wash for MSRA decolonization. Despite these positive results, essential oils have not been adopted in general medical practice. There have also been concerns raised that the use of sub lethal concentrations of tea tree oil may lead to the development of antibiotic resistance in human pathogens. (McMahon et al "Habituation to sub-lethal concentrations of tea tree oil (*Melaleuca Alternifolia*) is associated with reduced susceptibility to antibiotics in human pathogens", J. Antimicrobial Chemotherapy (2007) 59, 125-127).

Despite this broad spectrum activity, the antibacterial activity when compared to systemic antibiotics must be described as moderate at least. For example, one study compared the antimicrobial activity of the essential oil of *Artemisia iwayomogi*, a plant used in traditional Korean medicine, and its main compounds borneol, $\alpha$-terpineol, camphor, 1,8-cineole, $\beta$-carophyllene, terpinene-4-ol, with the antibiotics ampicillin and gentamicin. (Cha Jeong-Dan, "Chemical composition and antibacterial activity against oral bacteria by the essential oil of compared the antimicrobial activity of the essential oil of *Artemisia iwayomogi*", J. Bacteriology and Virology, 2007 37, No 3 129-136). Whilst borneol, $\alpha$-Terpineol, camphor, 1,8-cineole, $\beta$-carophyllene and terpinene-4-ol all showed inhibitory behaviour against a range of bacteria, the MIC (minimum inhibitory concentration) and MBC (minimum bacteriocidal concentration) were in the order of 0.4 mg/ml-3.2 mg/ml as compared to $2\times10^3$ mg/ml-$256\times10^{-3}$ mg/ml for ampicillin and gentamycin. In other words the MIC and MBC values for the essential oils and their components were in the order of 1000 times greater than for the systemic antibiotics.

For a systemic antibiotic to be effective the MIC/MBC values must be able to be reached at the site of infection. For example, administration of a 500 mg dose of ampicillin capsules results in an average peak blood serum level of approximately 3 µg/ml. A dose for a compound or composition having a MIC/MBC a thousand times that of ampicillin is clearly not only impractical but potentially toxic to the patient.

As mentioned above, the use of antibiotics has resulted in a range of antibiotic resistant organisms. This has been attributed to a range of factors such as overuse and misuse of prescription antibiotics, overuse of topical antiseptics such as triclosan and the wide use of antibiotics as growth promoters in animal feeds. The latter in particular is causing concern. It is estimated that 70% of the antibiotics in the United States are consumed by livestock. Governments around the world are investigating phasing out the use of antibiotics in animal production. Antibiotics are also widely used in cosmetic products and in food production. For example, many prepackaged precut foods are sprayed with antibacterial solutions to extend shelf life.

There is clearly a desire to be able to provide an alternative to the use of current antibacterial agents particularly in the animal feed industry.

Some essential oils are purported to have antiviral activity. However, the reports are generally limited to use in alternative medicine and home remedies. There is very little scientific support. Tea tree oil has been proposed as a topical agent for the treatment of herpes and there is some scientific support for this activity.

The present inventor has surprisingly discovered a synergistic monoterpenoid composition containing compounds that may be obtained from or derived from essential oils that has broad spectrum antibiotic activity and that, unlike conventional essential oils, may provide a viable alternative or adjunct to the use of current antibiotics.

SUMMARY OF THE INVENTION

1. According to a first broad form of the invention, there is provided a composition comprising;
   (a) 30%-80% of at least one compound having the formula 1

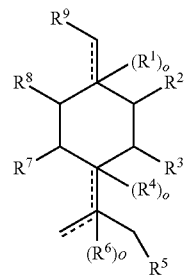

wherein ----- is ——— or ═══, but consecutive ----- cannot be ═══, the cyclohexane ring may be saturated or unsaturated with any degree of unsaturation provided that when a ----- attached to the ring is ═══ the ring carbon to which the ----- is attached is unsaturated;

one of $R^1, R^2, R^3, R^4, R^5, R^6, R^7, R^8$ or $R^9$ is OH, and each of the remaining $R^1, R^2, R^3, R^4, R^5, R^6, R^7, R^8$ and $R^9$ is H;

o is 0 when the ----- to which $R^1, R^4, R^5$ or $R^9$ is attached is ═══ and o is 1 when the ----- to which $R^1, R^4, R^5$ or $R^9$ is ———;

(b) 10% to 40% of at least one compound of formula 2

Formula 2

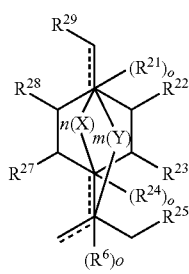

wherein ----- is ———, ═══ or

, but consecutive ----- cannot be ═══ or

;

the cyclohexane ring may be saturated or unsaturated with any degree of unsaturation provided that when a ----- attached to the ring is ═══ or

the ring carbon to which the ----- is attached is unsaturated;

X is —O— or —O—O—;
Y is —O— or —O—O— n is 0 or 1, m is 0 or 1, but n and m cannot both be 1 and neither n or m can be 1 if the ----- attached to the ring is ═══ or

$R^{21}, R^{22}, R^{23}, R^{24}, R^{25}, R^{26}, R^{27}, R^{28}$ or $R^{29}$ are each independently selected from H, OH, OOH, OC═OR, OR; or an adjacent pair of $R^{21}, R^{22}, R^{23}, R^{24}, R^{27}$ or $R^{28}$ may join to form an epoxide or

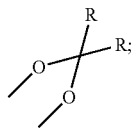

wherein any one of $R^{22}, R^{23}, R^{27}, R^{28}$ or $R^9$ may further be ═O, provided that ═O is attached to an unsaturated carbon; o is 0 when the ----- to which $R^{21}, R^{24}$ or $R^{26}$ is attached is ═══ or

and o is 1 when the ----- to which $R^{21}, R^{24}$ or $R^{26}$ is ——— and

R is a $C_1$ to $C_3$ alkyl;

wherein the compound contains at least two Oxygen atoms; and (c) from 0 to 20% of at least one compound selected from the group consisting of a sesquiterpene, a sesquiterpene alcohol, a sesquiterpene epoxide, p-cymene an oxygenated cyclohexane, an oxygenated cyclohexene, and a monoterpene, wherein the amount of any monoterpenes in the fraction does not exceed 5% of the total composition.

In the present specification and claims, the term % refers to the percentage as determined by gas chromatographic analysis, unless indicated otherwise. Gas chromatographic methods for the analysis of mixtures of terpenes and related compounds are well known in the art of natural product chemistry and aroma chemistry.

The present inventor has surprisingly discovered that the composition of the invention is effective against a broad range of bacteria at concentrations that may be considered suitable for therapy.

The compounds of formulas 1 and 2 include oxygenated derivatives of monoterpenes having a p-menthane skeleton. Monoterpenes are widely found in natural products and have the formula $C_{10}H_{16}$. The compounds of formulas 1 and 2 may be obtained or derived from known natural sources of monoterpenes or may be synthesized. Sources of monoterpenes and their oxygenated derivatives include but are not limited to eucalyptus oil, oil of cajeput, oil of camphor, oil of cardamom, tea tree oil, oil of cedar and oil of cypress. Suitable methods of extraction are known to those of skill in the art.

The oxygenated compounds of formula 1 and formula 2 may be obtained by oxidation of parent monoterpenes. Suitable starting monoterpenes include, ∝ pinene, β pinene, sabinene, myrcene, ∝ phellandrene, β phellandrene, ∝ terpinene, β terpinene, γ terpinene, limonene, ∝ limonene diepoxide and terpinolene. These compounds are naturally occurring and may be isolated from a variety of plant sources.

Many of these compounds are commercially available in an essentially pure form. Oxidation of monoterpenes is used to produce compounds for use in the flavour and perfumery industry. Oxidation of monoterpenes is well known in the field of organic flavour chemistry.

α-terpinene is a suitable starting material as it may readily be oxidised with molecular oxygen vis a diels alder cyclization of the 1,3-diene to produce the menth-2-ene, 1,4-endoperoxide (reaction 1 in Scheme 1 below). The peroxide is a useful intermediate as it may undergo further reaction with water to produce 1-hydroperoxy-4-hydroxy-menth-2-ene (reaction 2). Subsequent reduction with lithium hydroxide for example yields 1,4-dihydroxymenth-2-ene (reaction 3).

Terpinene-4-ol is also a suitable starting product and may be oxidised to 1,2,4-trihydroxy menthane by a number of reactions, one of which is as shown below in scheme 3 (Cristea, et al "Stereoselective trans-dihydroxylation of terpinen-4-ol: synthesis of some steriosomers of p-menthane-1,2,4-triol", Tetrahedron: Asymetry, 13, (9) 915-918).

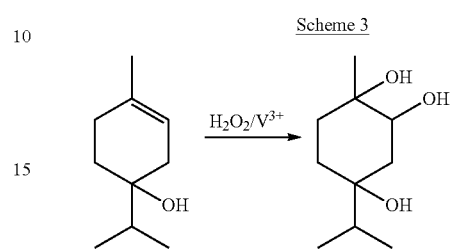

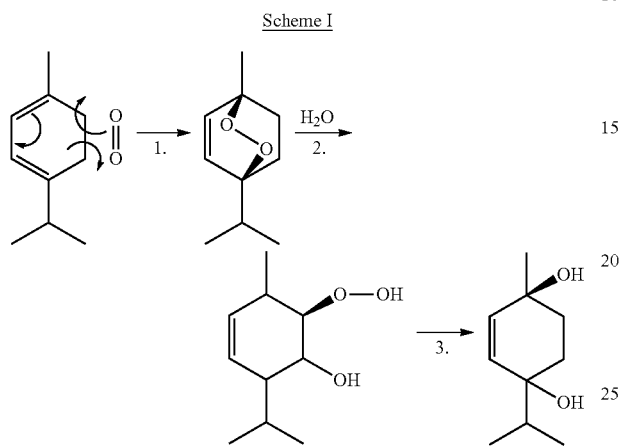

1,4-dihydroxymenth-2-ene can be prepared from ascaridole by first hydrolysing ascaridole to menth-2-ene-1,4-endoperoxide followed by reduction to give the product compound.

α-terpinene may also be oxidized with t-butyl chromate according to the procedure described by Suga et al "Stereochemical Studies of monoterpene compounds III. Stereochemistry and intramolecular hydrogen bonding of 1-hydroxy-p-menth-3-en-2-one and its reduction products, Bulletin of the Chemical Society of Japan, 41, 944-048 (1968). The reaction produces 1-hydroxy-p-menth-3-en-2-one (reaction 4) which may subsequently be hydrogenated (reaction 5) and reduced (reaction 6) or reduced (reaction 7) and hydrogenated (8) as shown in scheme 2 below.

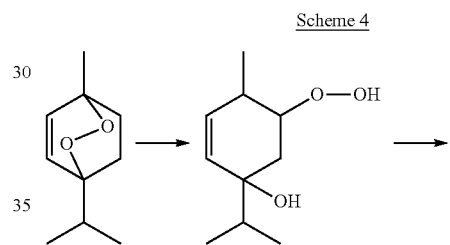

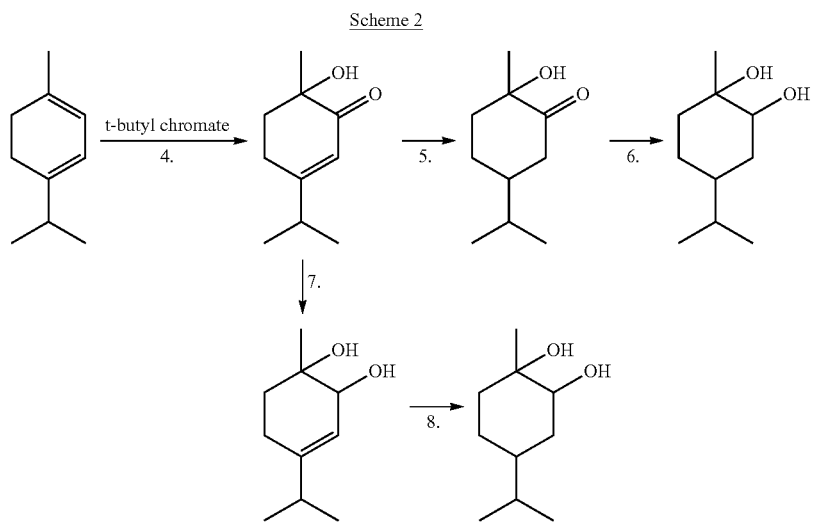

Oxidation of monoterpenes often results in a mixture of compounds. In the compositions and methods of the present invention, mixtures of compounds of the invention may be tolerated where components of the mixture either are inactive and non-toxic or present in very low concentrations. In some cases, it may not be necessary for the parent monoterpenes to be chemically or chirally pure.

Preferred compounds of formula 1 include aterpineol (1), β-terpineol (2), γ-terpineol (3), terpinene-4-ol (4), menthol (5), thymol (6), carvacrol (7), carveol (8), isopipertinol (9), perillyl alcohol (10), 8-hydroxy-p-cymene (11), isopulegol (12), limonene-10-ol (13) and dihydrocarceol (14) and 4-isopropyl-1-methylcyclohex-e-enol (15)

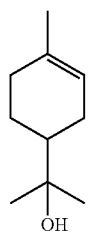

1

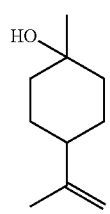

2

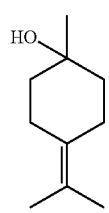

3

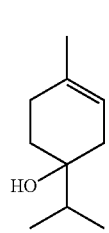

4

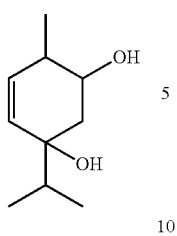

5

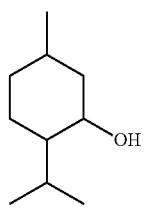

5

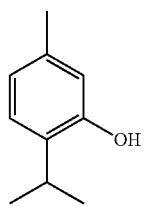

6

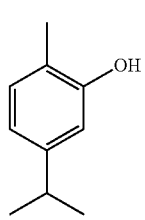

7

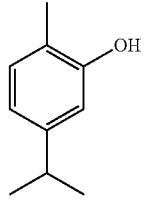

8

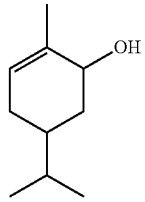

9

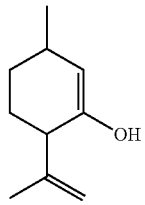

10

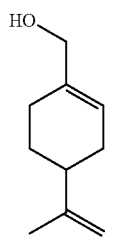

11

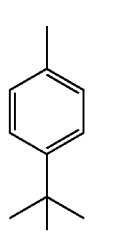

-continued

12

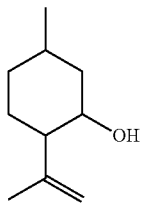

13

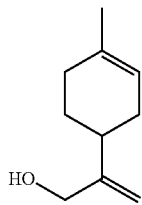

14

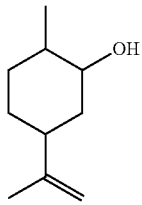

15

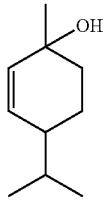

A preferred composition contains terpinene-4-ol as the major constituent. Terpinene-4-ol is found in nature and is a major constituent of the tea tree oil. Terpinene-4-ol is also available commercially in the racemic form, and as the R and S isomers. In tea tree oil the chiral purity has been found to be (+)-(4R)-∝ Terpineol 75% and (−)-4S-∝-Terpinen4-ol 25% (Burfiekd and Sheppard Hanger", "super Clone 88-<*elalecua Alternifolia*—what is its value?", http://atlanticinstitute.com/teatree.pdf). Preferably, terpinene-4-ol is present from about 40% to about 70%, preferably between about 45% to about 65%, preferably between about 48% to about 60% of the composition. Preferably the chiral purity of the terpinene-4-ol reflects that found in nature.

Preferably, the composition includes at least two compounds of formula 1. Preferably, the second compound is ∝-terpineol. A typical composition comprises between about 40% to about 70% preferably between about 45% to about 65%, preferably between about 48% to about 60% terpinene-4-ol and about 2% to about 15%, preferably between about 4% to about 12%, most preferably between about 5% to about 10% ∝-terpineol.

In one embodiment, the compounds of formula 1 consist essentially of terpinene-4-ol and α-terpineol.

As used herein, the phrase "consisting essentially of" limits the scope of the related disclosure or claim to the specified compounds, plus those that do not materially affect the basic and novel characteristic(s) of the disclosed and/or claimed subject matter. For example, a composition in which the compounds of formula 1 "consist essentially of" terpinene-4-ol and α-terpineol means that the recited compounds together represent at least 80%, or at least 85%, or at least 90% or at least 95% or at least 97.5% or at least 99% of the compounds of formula 1.

Suitable compounds of formula 2 include the following:

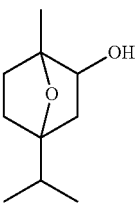 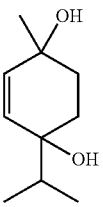 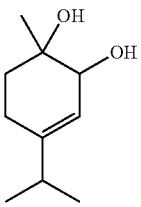

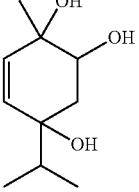 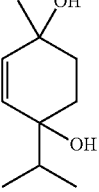 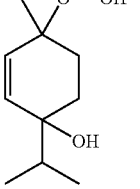

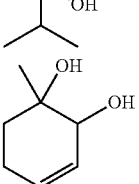 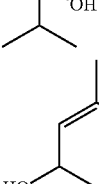 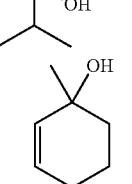

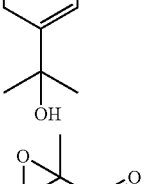 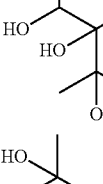 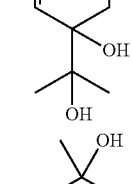

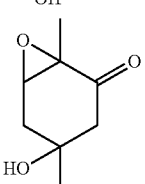 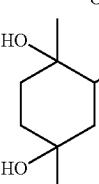 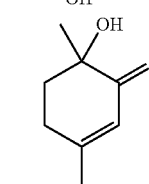

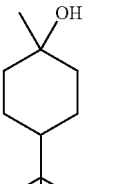 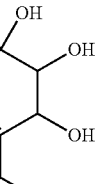 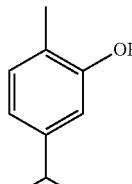

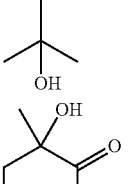 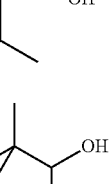 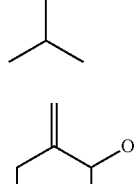

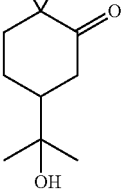 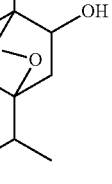 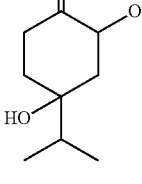

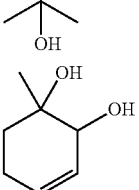 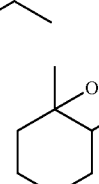 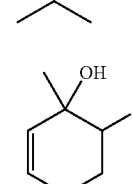

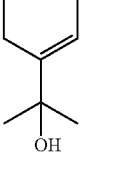 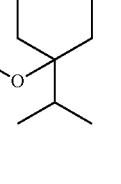 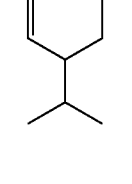

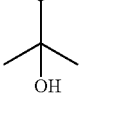 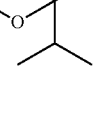 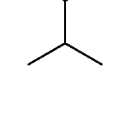

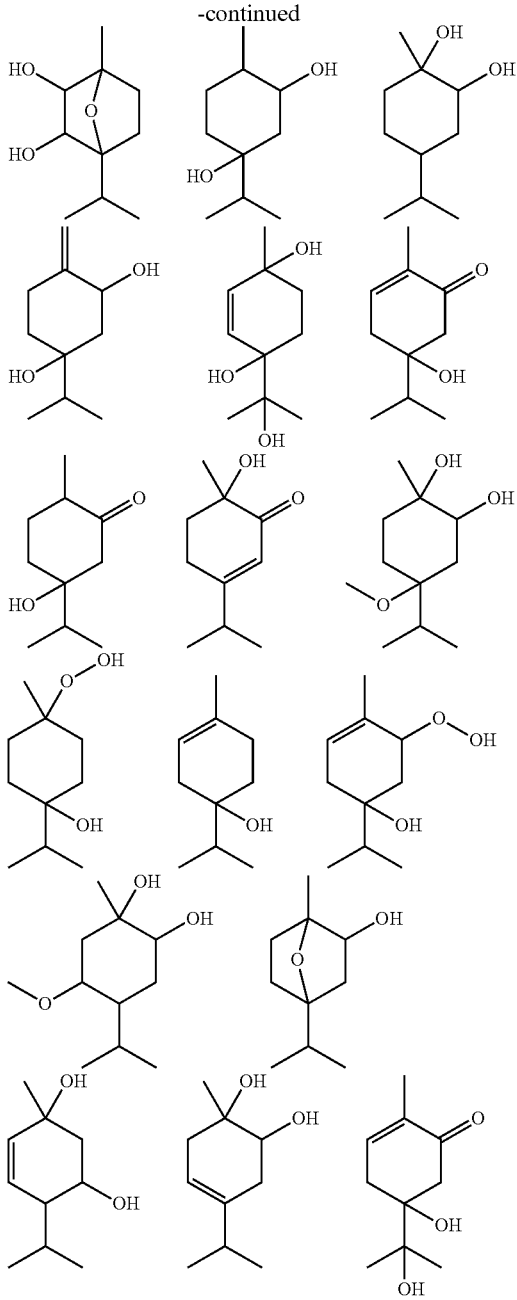

Preferably, the composition includes between about 10% to about 40%, preferably between about 15% to about 35%, preferably between about 20 to about 30% of di and tri-oxygenated compounds of formula 2.

Preferably the ratio of di-oxygenated to tr-oxygenated compounds is between about 1:1 to 5:1, preferably between about 1.5:1 to about 4:1, most preferably between about 2:1 to about 3:1.

An especially preferred composition comprises a fraction of compounds of formula 2 that comprises between about 1 to about 4%, preferably between about 2 to about 3% 2-hydroxy-1,4-cineole, between about 5% to about 15%, preferably between about 6% to about 12%, preferably between about 8% to about 10% 1,4-dihydroxy-menth-2-ene, between about 0.5% to about 5%, preferably between about 1% to about 4% 1,2-dihydroxy-menth-3-ene and between about 1 to about 10%, preferably between about 2% to about 8%, preferably between about 3% to about 6% 1,2,4-trihydroxy-menthane.

Some of these compounds are naturally occurring and are found in essential oils. 2-hydroxy-1,4-cineole may be found in extracts from *Hibiscus sabdariffa* L. It is also available commercially. Cymenol is found in sage essential oil (*Salvia officinalisl*) and essential oils of *Jumiperus* genus plants, 4,6-dihydroxy-p-menth-1-ene is found in oil of cumin, 1,4-dihydroxy-p-menth-2-ene in peppermint oil, 1,2-dihydroxy-p-menth-3-ene is found in *Ferula jaeschchkeana* and 1,2,4-trihydroxy-p-menthane is found in the oil of *Zanthoxylum bundruga* fruits.

The composition may also contain up to 20% of compounds other than those of formulas 1 and 2. These other compounds may include sesquiterpenes and oxygenated derivatives thereof, p-cymene an oxygenated cyclohexane, an oxygenated cyclohexene and low levels (less than 5%) of monoterpenes. It will be appreciated that any additional compounds should be non-toxic or be present in below toxic levels. In one embodiment, the composition can contain up to 15 wt % p-cymene.

The term oxygenated cyclohexene refers to any compound having a cyclohexene skeleton that is substituted with one or more oxygen groups such as =O, —OOH, or OH. The cyclohexene may further be substituted with a methyl or ethyl. A preferred compound is 4-methyl-4-hydroxy-cyclohex-3-enone.

The term oxygenated cyclohexane refers to any compound having a cyclohexane skeleton that is substituted with one or more oxygen groups such as =O, —OOH, or OH. The cyclohexane may further be substituted with a methyl or ethyl.

The composition may also contain up to 5% of a compound of formula 3;

Formula 3

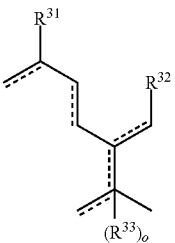

wherein ----- is ———, ═══ or

, but consecutive ----- cannot be ═══ or

;

$R^{31}$ and $R^{33}$ are each independently selected from H, OH, OOH, OC=OR, OR, $R^{31}$ may further be =O provided that the =O is not attached to an unsaturated carbon; $R^{32}$ is selected form the group consisting of CO, COOH, COH, COOR, COR; $R^{31}$ and $R^{32}$ may join to form a lactone;

o is 0 when the ══ to which $R^{10}$ is ─── or

and o is 1 when the carbon to which $R^{33}$ is – and
R is a $C_1$ to $C_3$ alkyl.

The compounds of formula 3 may be formed by an oxidative ring opening reaction of a parent monoterpene. This may occur as a by product of the oxidation reaction that produces compounds of formula 1. Especially preferred compounds include cis and/or trans 6-oxo-3-isopropyl-hept-2-enal and 6-oxo-3-isopropylheptenoic acid.

Stereoisomers:

Certain compounds of the invention contain chiral centres. Both racemic and diasteromeric mixtures, as well as the individual optical isomers isolated or synthesized, substantially free of their enantiomeric or diastereomeric partners, are all within the scope of the invention. The racemic mixtures may be separated into their individual, substantially optically pure isomers through well-known techniques, such as the separation of diastereomeric salts formed with optically active adjuncts, e.g., acids or bases followed by conversion back to the optically active substances. The desired optical isomer may be synthesized by means of stereospecific reactions, beginning with the appropriate stereoisomer of the desired starting material.

Prodrugs:

Prodrugs of the compounds of the invention are also contemplated. The terms "pro-drug" and "prodrug" are used interchangeably herein and refer to any compound which releases an active parent compound according to Formula 1, 2 or 2a in vivo when such prodrug is administered to an animal. Prodrugs may be prepared by modifying one or more functional group(s) present in the compound of Formula 1 or 2 in such a way that the modification(s) may be cleaved in vivo to release the parent compound.

Prodrugs include compounds of Formulas 1, 2 or 3 wherein a hydroxy, carboxy or carbonyl group in a compound of Formulas 1, 2 or 3 is bonded to any group that may be cleaved in vivo to regenerate the free hydroxyl group. Examples of prodrugs include, but are not limited to, esters (e.g., acetate, dialkylaminoacetates, formates, phosphates, sulfates, and benzoate derivatives) of hydroxy functional groups and esters groups (e.g. ethyl esters, morpholinoethanol esters) of carboxyl functional groups, oximes, acetals, ketals and enol esters of ketone and aldehyde functional groups in compounds.

The pharmaceutical compositions of the present invention can be manufactured by methods well known in the art such as conventional mixing, dissolving, encapsulating, lyophilizing or emulsifying, among others. The compositions can be in the form of, for example, granules, powders, tablets, capsules, syrup, suppositories, injections, emulsions, elixirs, suspensions or solutions. The instant compositions can be formulated for various routes of administration, for example, by oral administration, by transmucosal administration, by rectal administration, or subcutaneous administration as well as intrathecal, intravenous, intramuscular, intraperitoneal, intranasal, intraocular or intraventricular injection. The compound or compounds of the instant invention can also be administered in a local rather than a systemic fashion, such as injection as a sustained release formulation. The following dosage forms are given by way of example and should not be construed as limiting the instant invention.

For oral, buccal, and sublingual administration, powders, suspensions, granules, tablets, pills, capsules, gelcaps, and caplets are acceptable as solid dosage forms. These can be prepared, for example, by mixing one or more compounds of the instant invention, or pharmaceutically acceptable salts or tautomers thereof, with at least one additive or excipient such as a starch or other additive. Suitable additives or excipients are sucrose, lactose, cellulose sugar, mannitol, maltitol, dextran, sorbitol, starch, agar, alginates, chitins, chitosans, pectins, tragacanth gum, gum arabic, gelatins, collagens, casein, albumin, synthetic or semi-synthetic polymers or glycerides, methyl cellulose, hydroxypropylmethyl-cellulose, and/or polyvinylpyrrolidone. Optionally, oral dosage forms can contain other ingredients to aid in administration, such as an inactive diluent, or lubricants such as magnesium stearate, or preservatives such as paraben or sorbic acid, or anti-oxidants such as ascorbic acid, tocopherol or cysteine, a disintegrating agent, binders, thickeners, buffers, sweeteners, flavoring agents or perfuming agents. Additionally, dyestuffs or pigments may be added for identification. Tablets and pills may be further treated with suitable coating materials known in the art.

Liquid dosage forms for oral administration may be in the form of pharmaceutically acceptable emulsions, syrups, elixirs, suspensions, slurries and solutions, which may contain an inactive diluent, such as water. Pharmaceutical formulations may be prepared as liquid suspensions or solutions using a sterile liquid, such as, but not limited to, an oil, water, an alcohol, and combinations of these. Pharmaceutically suitable surfactants, suspending agents, emulsifying agents, may be added for oral or parenteral administration.

For nasal or buccal administration, the pharmaceutical formulations may be a spray or aerosol containing and appropriate solvents and optionally other compounds such as, but not limited to, stabilizers, antimicrobial agents, antioxidants, pH modifiers, surfactants, bioavailability modifiers and combinations of these. A propellant for an aerosol formulation may include compressed air, nitrogen, carbon dioxide, or a hydrocarbon based low boiling solvent. The compound or compounds of the instant invention are conveniently delivered in the form of an aerosol spray presentation from a nebulizer or the like.

Injectable dosage forms generally include aqueous suspensions or oil suspensions which may be prepared using a suitable dispersant or wetting agent and a suspending agent. Injectable forms may be in solution phase or in the form of a suspension, which is prepared with a solvent or diluent. Acceptable solvents or vehicles include sterilized water, Ringer's solution, or an isotonic aqueous saline solution. Alternatively, sterile oils may be employed as solvents or suspending agents. Preferably, the oil or fatty acid is nonvolatile, including natural or synthetic oils, fatty acids, mono-, di- or tri-glycerides.

For injection, the formulations may optionally contain stabilizers, pH modifiers, surfactants, bioavailability modifiers and combinations of these. The compounds may be formulated for parenteral administration by injection such as by bolus injection or continuous infusion. A unit dosage form for injection may be in ampoules or in multi-dose containers.

For rectal administration, the pharmaceutical formulations may be in the form of a suppository, an ointment, an enema, a tablet or a cream for release of compound in the intestines, sigmoid flexure and/or rectum. Rectal suppositories are prepared by mixing one or more compounds of the instant invention, or pharmaceutically acceptable salts or tautomers of the compound, with acceptable vehicles, for example, cocoa butter or polyethylene glycol, which is present in a solid phase at normal storing temperatures, and present in a liquid phase at those temperatures suitable to release a drug inside the body, such as in the rectum. Oils may also be employed in the preparation of formulations of the soft gelatin type and suppositories. Water, saline, aqueous dextrose and related sugar solutions, and glycerols may be employed in the preparation of suspension formulations which may also contain suspending agents such as pectins, carbomers, methyl cellulose, hydroxypropyl cellulose or carboxymethyl cellulose, as well as buffers and preservatives.

The compounds may also be administered dermally. It has been observed that the compounds are readily absorbed through the skin such that dermal uptake directly into the lymphatic system by dermal application about the lymph nodes is possible.

The terms "effective amount" and "therapeutically effective amount" of a compound as used herein mean a sufficient amount of the compound or a mixture of one or more thereof, to provide the desired therapeutic or physiological effect or outcome. Undesirable effects, e.g. side effects, are sometimes manifested along with the desired therapeutic effect; hence, a practitioner balances the potential benefits against the potential risks in determining what is an appropriate "effective amount". The exact amount required will vary from subject to subject, depending on the species, age and general condition of the subject, mode of administration and the like. Thus, it may not be possible to specify an exact "effective amount". However, an appropriate "effective amount" in any individual case may be determined by one of ordinary skill in the art using only routine experimentation.

DETAILED DESCRIPTION OF THE INVENTION

EXAMPLE 1

A composition was prepared having the following composition and allocated the reference MJR-1

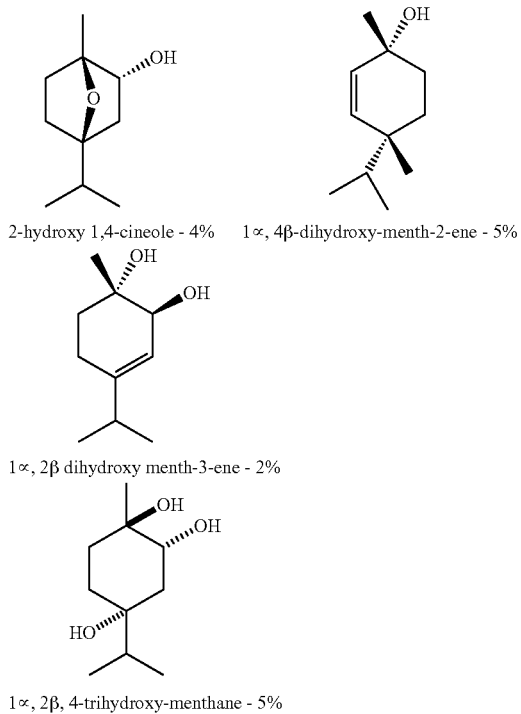

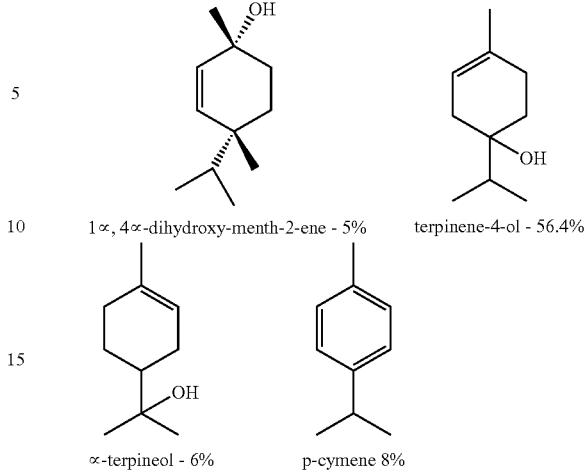

The balance of the composition is contains minor amounts of compounds of formula 1 and formula 2 and also minor amounts of sesquiterpenes.

1. Phase 1 Trials

Study Design

Twenty nine subjects were divided into three equal dosing groups of 5 males and 4-5 females. The subjects were aged between 19 to 53 years of age with normal body weight. The three groups were subjected to the following dosage regimes of an oral capsular dose of the composition of Example 1;

Group 1—a single 600 mg dose after a meal; a single 750 mg dose after a meal and three 300 mg doses at 8 hour intervals for 5 days.

Results

The effect of a single dose on the vital body parameters, systolic and diastolic blood pressures and heart rate at one and two hours after administration was observed. No clinically significant changes were observed.

Urine chemistry, urine sediments, blood chemistry and haematological profiles were measured prior to dosing and at 14 days post dosing. The results showed that after all dosage regimes, urine sediments, levels of urine, blood chemistries and haematological profiles were in normal values. These findings show that there was no apparent harm to the liver where the total levels of total and direct biliruben, SGOT and alkaline phosphatase in the blood were in normal ranges and there was no biliruben nor urobilin found in urine. Similar results were obtained for the kidneys where the levels of total protein albumin, blood urea nitrogen (BUN) and creatinine in blood were normal and no protein, blood cells nor leucocytes were found in the urine. The absence of glucose and ketone bodies in the urine also indicted that 600 mg of the inventive composition did not affect glycogeniesis as well. Hematological profiles (particularly the levels of white and red blood cells, haemoglobin, hematocrtite, thrombocyte (platelets) and coagulation time of the subjects were also unaffected by the doses. Further there was no production of Ca oxalate, triphosphate or uric acid crystals in the urine.

The conclusion that can be made from this trial is that the composition of Example 1 is well tolerated in subjects and is not likely to affect vital organs such as liver, kidney and hematology and it did not cause crystaluria.

EXAMPLE 2

Comparative trials were conducted to assess the difference in the antimicrobial activity of conventional *Melaleuca* oil (TTO), MAC and purified (98.9%) Terpinene-4-ol on a number of different microorganisms.

*Staphylococcus aureaus* is a facultatively anaerobic, gram-positive bacteria found on the skin of normal humans. It can cause a wide range of infections and a major cause of hospital acquired infections. *Escerichia coli* is a gram negative rod shaped bacterium. *Pseudomonas aeruginosa* is a gram negative rod shaped bacteria that it responsible for a range of hospital acquired infections. *Salmonella typhimurium* is a gram negative rod shaped bacteria responsible for food borne illness. *Listeria monocytogenes* is gram positive and rod shaped. It is one of the most virulent food borne pathogens. The experiments were carried out on 10% water solubilised solutions using Vitamin E as an emulsifier. TTO was chosen as comparison oil as TTO has a high content of terpinene-4-ol, the major constituent of the preferred composition of the present invention. As discussed above 5% solutions of TTO have been proposed as decolonization washes for MRSA.

Culture Preparation
1. Stock culture was streaked onto the surface of a Tryptone soya agar plate and incubated at 36° C. for 18 to 24 hours.
2. A second subculture was prepared from the first subculture by streaking onto the surface of a fresh agar plate and incubating 18 to 24 hours.
3. Approximately 5-10 mL of sterile water was added to a sterile tube.
4. Loopfuls of the working culture (second subculture) were transferred into the diluents.
5. The microbial tests suspension was counted by serial dilution using 1% Petpone solution and plating duplicate dilutions into separate Petri dishes.
6. The plates were pured with 12 to 15 ml of molten Truptone soys agar cooled to approximately 46° C. The agar was allowed to set and incubated at 36° C. for 48 hours.
7. The number of cfu/mL in the tests suspension was calculated.

Test Procedure

Procedures were carried out at room temperature. The recovery time was 30 minutes and 24 hours.
1. The challenge organism stock was aseptically added to the organism stock suspension to deionized water and water soluble vitamin E. The water soluble form of vitamin E was added as a surfactant to provide a dispersion of the water insoluble compounds of the composition in the aqueous medium. A water soluble form of vitamin E is manufactured by BASF under the trade name SoluE.
2. The test product was added to the challenge mix.
3. The mixture was placed in a shaker for 30 min+/−30 sec.
4. At the end of the contact time, 1 mL of the test mixture was pipetted into a tube containing 9 mL of nutrient broth with 3% tween 80.
5. A 1 mL sample of the neutralized mixture (nutrient broth & tween+challenge test suspension was plated onto nutrient Petri dishes.
6. Serial dilution in 0.1% peptone solution were performed and 1 mL portions ere plate in duplicate.
7. The plates were overlayed with molten Tryptone soya Agar and incubated at 36+/−1° C. for 48 hours.
8. The number of cfu/mL in the test mixture was calculated.
9. Steps 4 to 7 were repeated after 24 hours.

Test Results

Log reduction of challenge organisms after 24 hours contact time was calculated using the formula:

Log $R$=Log $A$−Log $B$

Where R=Reduction
A=number of bacteria in the test solution
B=the number of bacteria recovered from the inoculated test solution incubated over the desired contact time.

The effective concentration that killed 99.9% of the test bacteria (MBC) is determined. The results are summarized provided in table 1 below.

TABLE 1

| Bacteria | TTO Terpinen-4-ol 49% | Terpinene-4-ol 98.9% | Composition of Example 1 Terpinene-4-ol 59% |
|---|---|---|---|
| *S. aureus* | 1000 ppm | 250 ppm | 10 ppm |
| *E. coli* | No level (>1000 ppm) | No level (>500 ppm) | 10 ppm |
| *P. aeruginosa* | No level (>1000 ppm) | No level (>500 ppm) | 250 ppm |
| *Salmonella typhimurium* ATCC 13311 | No level (>1000 ppm) | No level (>500 ppm) | 10 ppm |
| *Listeria monocytogenes* ACM 98 | No level (>1000 ppm) | No level (>500 ppm) | 10 ppm |

The table also shows the different levels of terpinene-4-ol in each trial. Tea tree oil has 49% terpinene-4-ol, such that when the respective MBC's are corrected according to tea tree oil content, the MBC values for *S. Arues* become comparable i.e. about 500 ppm for TTO compared with 250 ppm for terpinene-4-ol). Making the same calculation for the composition of the present invention the MBC value changes form 10 ppm to 16.76 ppm. Clearly the observed difference in efficacy with between tea tree oil and that of the inventive composition cannot be attributed to the slightly higher level of terpinene-4-ol.

The values for the compounds of the present invention are significantly below that for TTO and terpinene-4-ol which strongly suggests a synergistic effect. It should be noted that MCC values of 10 ppm are within the ranges considered acceptable for systemic antibiotics. For example, most bacteria are considered to be resistant to a particular antibiotic when the MCC value is in the order of 30 ppm or greater.

The composition of the present invention also contains p-cymene and ∝-terpineol. Both of these compounds are present in TTO. The content of each in the present composition is slightly higher than in TTO. P-cymene is typically present in TTO at about 1.3% and ∝-terpineol about 20.9% as compared with 6.5% and 8%. Although the present inventor did not investigate the antibacterial activity of these compounds, this has been done a number of times previously by other authors. One example is Caron and Riley, "Antimicrobial activity of the major components of the essential oil of *Melaleuca Alternifolia*", J. Applied Bacteriology 1995 78, 264-269. A summary of the results for MIC a (minimal inhibitory concentration) and MBC values obtained by the broth dilution technique is summarised below in Table 2.

TABLE 2

| Compound | E. coli MIC (v/v %) ppm | E. coli MBC (v/v %) ppm | Staph. aureus MIC (v/v %) ppm | Staph. aureus MBC (v/v %) ppm |
|---|---|---|---|---|
| Terpinene-4-ol | 0.06 600 | 0.06 600 | 0.25 2500 | 0.25 2500 |
| ∝-terpineol | 0.06 600 | 0.06 600 | 0.25 2500 | 0.25 2500 |
| p-cymene | >8.0 No level | >8.0 No level | >8.0 No level | >8.0 No level |

It is acknowledged that it is difficult to compare results obtained under different experimental conditions. This difficulty is As noted in this paper, difficulties were experienced in relation to solubility and turbidity problems. In particular, the water insolubility of some of these compounds makes accurate determinations difficult and the manner in which each investigator addresses these problems can influence the final result. Nevertheless, it is reasonable to expect that there is internal consistency between individual reports.

Turning now to Table 2, it can be seen that the MIC values of terpinene-4-ol are different to that in Table 1. This can be attributed to different experimental design. However, the data does show that the activity of ∝-terpineol is similar to that for terpinene-4-ol and that p-cymene has no effect at all.

The remaining compounds are di or tri-oxygenated monoterpene derivatives. The present inventor is unaware of any reported antibacterial activity of these compounds.

Without wishing to be bound by theory, the inventor believes that the composition of the present invention exhibits synergistic activity.

EXAMPLE 3

A further study was conducted to assess the effectiveness of antimicrobial activity of the inventive composition against *Clostridium difficile*. *Clostridium difficile* is an anaerobic bacteria that causes diarrhoea and other intestinal diseases when competing bacteria are wiped out by antibiotics.

Experimental Procedure

*Clostridium* challenge microorganisms *Clostridium difficile* ACM 5047 were incubated at 37° C. for 24 hours prior to subculturing onto Columbia Horse Blood Agar using the spread plate method. Columbia HBA plates were incubated aerobically at 37° C. for 2 days and visible colonies counted.

A 10v/v % sample of the composition of the invention was prepared in water. The 10v/v % solution was diluted with sterile deionized water and 10 ml of each test concentration was added to a sterile test tube. 100 μml of tests culture was added to each test dilution.

The results are shown in the following Table 3.

TABLE 3

| Organism | Inoculum (cfu) | Recovery count (cfu/ml) with an active product concentration of 50 ppm | Recovery count (cfu/ml) with an active product concentration of 25 ppm | Recovery count (cfu/ml) with an active product concentration of 10 ppm |
|---|---|---|---|---|
| Clostridium difficile | $3.8 \times 10^5$ | 48 38 | | 11 5 |

EXAMPLE 4

Further studies were conducted to assess the kill time on *Proteus vulgaris* NCTC 4635 and *Escherichia coli* NCTC 9001. *Proteus vulgaris* is a rod-shaped gram negative bacteria that can cause urinary tract and wound infections.

| Organism | Composition concentration | Inoculum count (cfu) | Time after inoculation/ minutes | Recover count (cfu per mL) Control | Test |
|---|---|---|---|---|---|
| Proteus vulgarisl NCTC 4635 | 50 ppm | $1.4 \times 10^6$ | 5 15 30 | $6.1 \times 10^6$ $4.8 \times 10^6$ $6.3 \times 10^6$ | <10 <10 <10 |
| Proteus vulgaris NCTC 4635 | 25 ppm | $1.4 \times 10^6$ | 5 15 30 | $6.1 \times 10^6$ $4.8 \times 10^6$ $6.3 \times 10^6$ | $2.6 \times 10^6$ $5.3 \times 10^2$ <10 |
| Escherichia coli NCTC 9001 | 50 ppm | $7.0 \times 10^5$ | 5 15 30 | $8.6 \times 10^6$ $6.1 \times 10^5$ $5.1 \times 10^5$ | $2.4 \times 10^5$ $6.4 \times 10^3$ $1.3 \times 10^2$ |

The above results show that the composition of the invention is effective at rapidly killing 99.9% of the bacteria at concentrations of 50 ppm and 25 ppm. The previous results for *E. coli* above show that 99.9% are killed in 24 hours at 10 ppm.

It may be seen that the composition of the present invention is surprisingly effective against a wide range of organisms. Its effectiveness could not have been predicted based upon the known activity of the individual components thus suggesting a synergistic relationship. For example, tea tree oil which has a similar, although slightly lower level of terpinene-4-ol has been reported to have MIC's for *E. Coli*, 0.5% (5000 ppm), *S. Aureus*, 0.5% (5000 ppm) and *Salmonella* spp., 0.25% (2500 ppm), a determined by the broth dilution method (MaMahon et al). This may be compared with the compulsion of Example 1 which showed a MCC of 10 ppm (0.0011%) for each organism. Although direct comparisons between different tests conditions cannot be made, it is believed that a factor of 250 and 500 must be considered to be significant and cannot be explained by different challenge conditions.

It will be appreciated that various other changes and modifications may be made to the present invention as described and claimed herein without departing form the spirit and scope thereof.

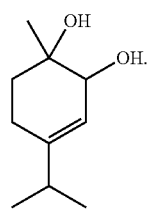

16. The composition of claim 4, comprising each of the compounds
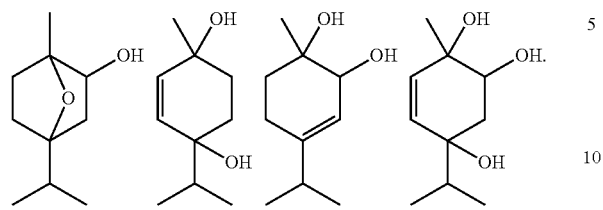

The invention claimed is:

1. A composition comprising;

(a) 30%-80% of at least one compound having the formula (I)

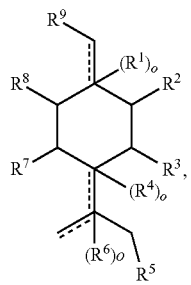

wherein ===== is ———— or ====, but consecutive ===== cannot be ====; the cyclohexane ring may be saturated or unsaturated with any degree of unsaturation provided that when a ===== attached to the ring is ==== the ring carbon to which the ===== is attached is unsaturated;

one of $R^1$, $R^2$, $R^3$, $R^4$, $R^5$, $R^6$, $R^7$, $R^8$ or $R^9$ is OH, and each of the remaining $R^1$, $R^2$, $R^3$, $R^4$, $R^5$, $R^6$, $R^7$, $R^8$ and $R^9$ is H;

o is 0 when the ===== to which $R^1$, $R^4$, $R^5$ or $R^9$ is attached is ==== and o is 1 when the ===== to which $R^1$, $R^4$, $R^5$ or $R^9$ is ———— ;

wherein the at least two compounds of formula I consist essentially of terpinene-4-ol and α-terpineol;

(b) 10% to 40% of at least one compound of formula (II)

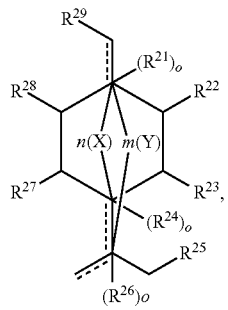

wherein ===== is ————, ==== or

, but consecutive ===== cannot be ==== or

;

the cyclohexane ring may be saturated or unsaturated with any degree of unsaturation provided that when a ===== attached to the ring is ==== or

the ring carbon to which the ===== is attached is unsaturated;

X is —O— or —O—O—;
Y is —O— or —O—O—
n is 0 or 1, m is 0 or 1, but n and m cannot both be 1 and neither n or m can be 1 if the ===== attached to the ring is ==== or

$R^{21}$, $R^{22}$, $R^{23}$, $R^{24}$, $R^{25}$, $R^{26}$, $R^{27}$, $R^{28}$ or $R^{29}$ are each independently selected from H, OH, OOH, OC=OR, OR; or an adjacent pair of $R^{21}$, $R^{22}$, $R^{23}$, $R^{24}$, $R^{27}$ or $R^{28}$ may join to form an epoxide or

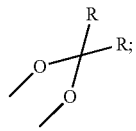

wherein any one of $R^{22}$, $R^{23}$, $R^{27}$, $R^{28}$ or $R^9$ may further be =O, provided that =O is attached to an unsaturated carbon; o is 0 when the to ===== which $R^{21}$, $R^{24}$ or $R^{26}$ is attached is ==== or

and o is 1 when the ===== to which $R^{21}$, $R^{24}$ or $R^{26}$ is ———— and R is a $C_1$ to $C_3$ alkyl;

wherein the at least one compound of formula 2 comprises between about 1% to about 4% 2-hydroxy-1,4-cineole; between about 5% to about 15% 1,4-dihydroxy-menth-2-ene; between about 0.5% to about 5% 1,2-dihydroxy-menth-3-ene and between about 1% to about 10% 1,2,4-trihydroxy-menthane; and (c) from 0 to 20% of at least one compound selected from the group consisting of an sesquiterpene, a sesquiterpene alcohol, a sesquiterpene epoxide, p-cymene, an oxygenated cyclohexane, a oxygenated cyclohexene and a monoterpene, wherein the amount of any monoterpenes in the fraction does not exceed 5% of the total composition.

2. The composition of claim 1 comprising between about 40 and about 70% terpinene-4-ol and about 4% to about 15% α-terpinene.

3. The composition of claim 1, which comprises at least one further compound formula (II) selected from the following compounds;
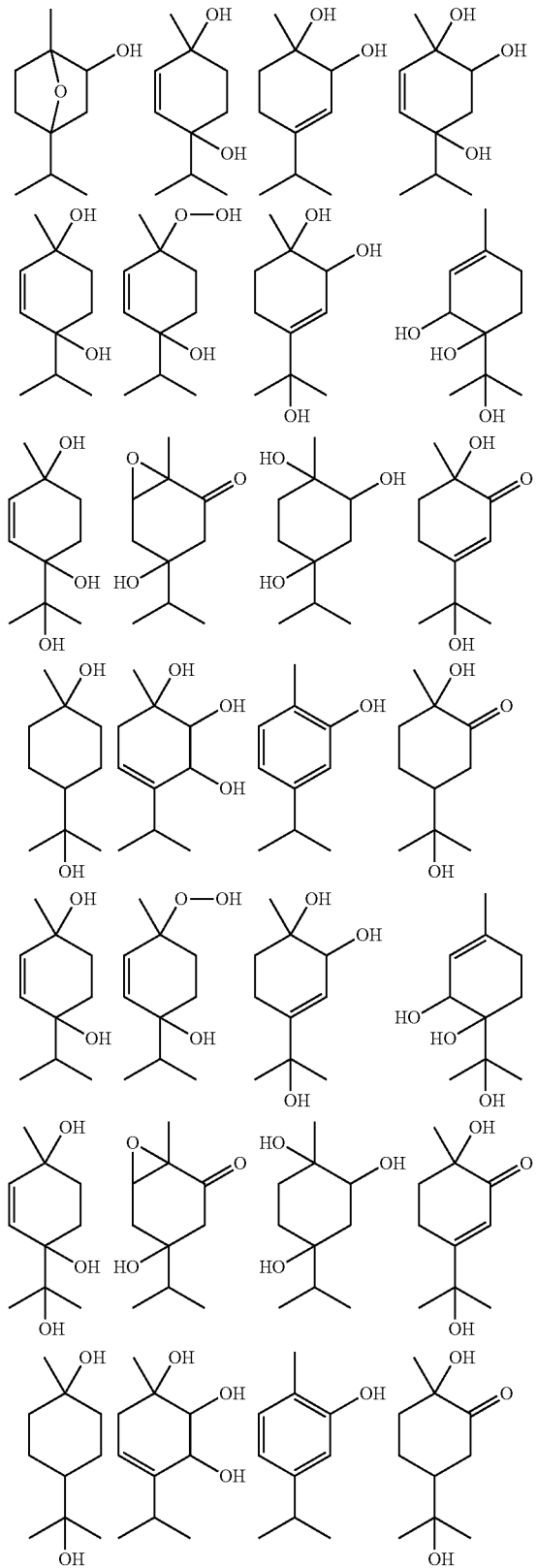
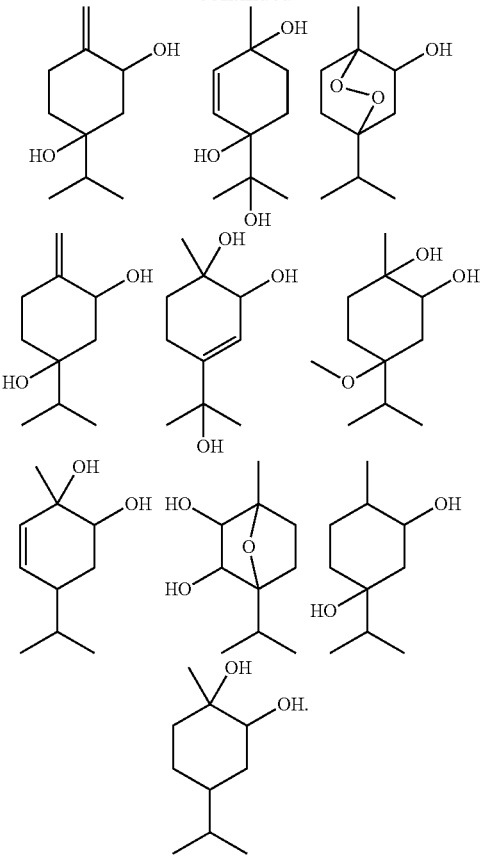
4. A composition comprising between about 40% and about 70% terpinene-4-ol, between about 4% to about 15% α-terpineol and between about 10% to about 40% of at least two compounds selected from the group consisting of:
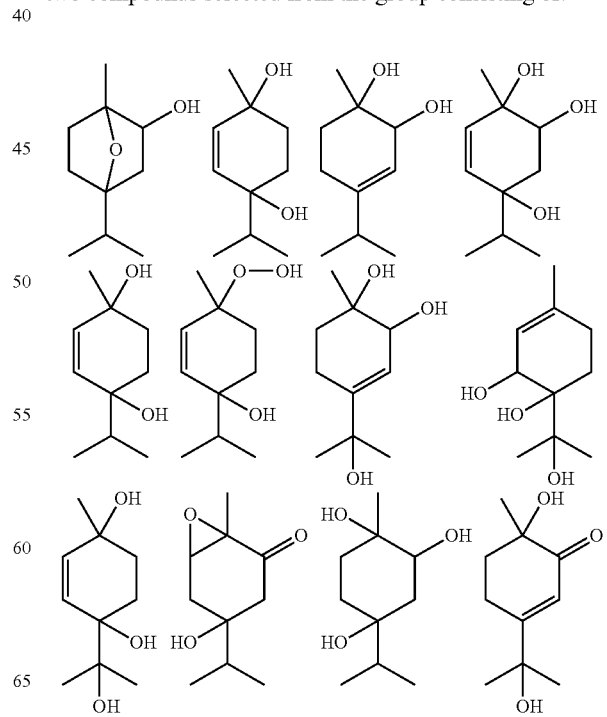

-continued

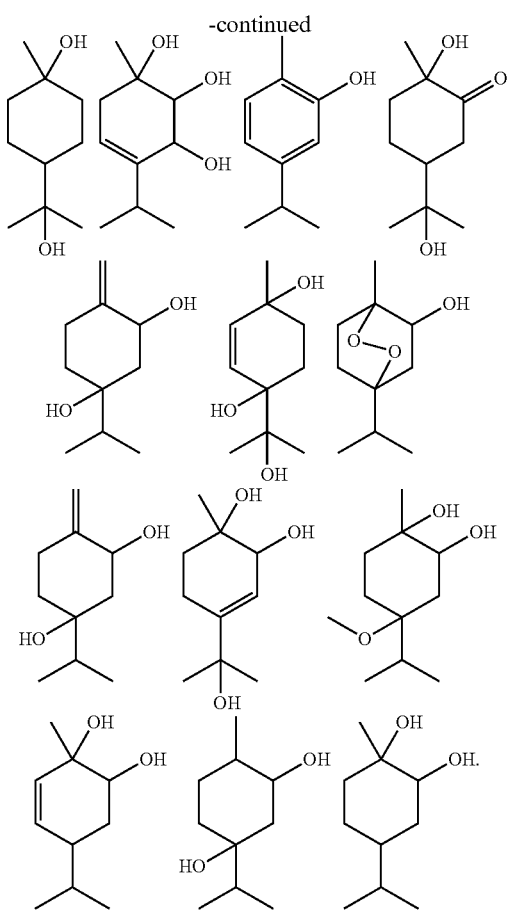

5. The composition of claim 4, wherein at least one of said at least two compounds has two oxygen atoms and at least one of said at least two compounds has three oxygen atoms, wherein the ratio of the at least one compound having two oxygen atoms to the at least one compound having three oxygen atoms is between about 1:1 to 5:1.

6. The composition of claim 4, further comprising about 7% to about 15% p-cymene.

7. The composition of claim 4, further comprising at least one sesquiterpene.

8. The composition of claim 7, wherein the at least one sesquiterpene is selected from the group consisting of isoledene, calamene, ledene, allo-aromadendrene, aromadendrene.

9. The composition of claim 4, further comprising up to 5% of a compound of the formula (III);

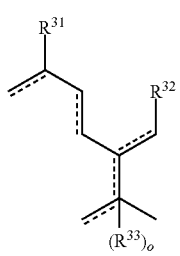

Formula 3 wherein ===== is ———, ==== or

, but consecutive ===== cannot be ==== or

;

$R^{31}$ and $R^{33}$ are each independently selected from H, OH, OOH, OC=OR, OR, $R^{31}$ may further be =O provided that the =O is not attached to an unsaturated carbon; $R^{32}$ is selected form the group consisting of CO, COOH, COH, COOR, COR; $R^{31}$ and $R^{32}$ may join to form a lactone;

o is 0 when the ===== to which $R^{10}$ is ==== or

and o is 1 when the carbon to which $R^{33}$ is ——— and R is a $C_1$ to $C_3$ alkyl.

10. The composition of claim 4, wherein the composition comprises between about 15% to about 35% of at the at least two compounds.

11. The composition of claim 4, wherein the composition comprises between about 20% to about 30% of at said at least two compounds.

12. The composition of claim 4, wherein least one of said at least two compounds has two oxygen atoms and at least one of said at least two compounds has three oxygen atoms, wherein the ratio of the at least one compound having two oxygen atoms to the at least one compound having three oxygen atoms is between about 1.5:1 to about 4:1.

13. The composition of claim 4, wherein least one of said at least two compounds has two oxygen atoms and at least one of said at least two compounds has three oxygen atoms, wherein the ratio of the at least one compound having two oxygen atoms to the at least one compound having three oxygen atoms is between about 2:1 to about 3:1.

14. The composition of claim 1, wherein the at least one compound of formula 2 comprises between about 2% to about 3% 2-hydroxy-1,4-cineole; between about 6% to about 12% 1,4-dihydroxy-menth-2-en; between about 1% to about 4% 1,2-dihydroxy-menth-3-ene and between about 3% to about 6% 1,2,4-trihydroxy-menthane.

15. The composition of claim 4, wherein at least one of the compounds is